United States Patent [19]
Thaler et al.

[11] Patent Number: 5,637,496
[45] Date of Patent: Jun. 10, 1997

[54] DEVICE AND METHOD FOR CONVEYING AND SEPARATING A SUSPENSION WITH BIOLOGICAL CELLS OR MICRO-ORGANISMS

[75] Inventors: Thomas Thaler, Zürich, Switzerland; Gerhard Klement, Warmond, Netherlands

[73] Assignee: B. Braun Biotech International mbH, Melsungen, Germany

[21] Appl. No.: 508,618

[22] Filed: Jul. 28, 1995

Related U.S. Application Data

[63] Continuation of Ser. No. 87,182, Jul. 2, 1993, abandoned.
[51] Int. Cl.$^6$ ........................................... C12M 3/00
[52] U.S. Cl. .................. 435/261; 435/287.3; 435/308.1
[58] Field of Search ...................... 435/261, 287.3, 435/307.1, 308.1, 813, 70.21, 70.3, 71.1, 240.1, 240.23, 240.24, 243; 210/150, 175, 232

[56] References Cited

U.S. PATENT DOCUMENTS 5,126,269  6/1992  Fike et al. ........................ 435/308.1
5,164,081  11/1992 Nichols et al. .................... 210/232

*Primary Examiner*—George Yeung
*Attorney, Agent, or Firm*—Michael J. Striker

[57] ABSTRACT

The device for conveying and separating a suspension with biological cells or micro-organisms in biological processes has a rotating separating element in a surrounding reaction space with a flow space which is in the form of a rotational gap, an inlet opening, an inner outlet opening for the cell-free medium, an outer through opening and an exit opening for the suspension. The distance R4 of the exit opening from the axis of rotation is greater than the distance R1 of the inlet opening, and the distance R3 of the through opening is greater than the distance R2 of the inner outlet opening. The suspension can thus be conveyed in the flow space and the cells efficiently separated at the same time. The device is particularly suitable for continuous operation with sensitive mammal cells.

28 Claims, 7 Drawing Sheets

DEVICE AND METHOD FOR CONVEYING AND SEPARATING A SUSPENSION WITH BIOLOGICAL CELLS OR MICRO-ORGANISMS

This is a continuation of application Ser. No. 08/087,182 filed Jul. 2, 1993, now abandoned.

BACKGROUND OF THE INVENTION

The invention relates to a device with a rotating separating element and a method for conveying and separating a suspension with biological cells or microorganisms in biological processes. It also relates to a bioreactor with a conveying and separating device of this kind. Continuous cell separation or particle separation of human, animal, plant or hybrid culls, micro-organisms or of carriers populated with cells (micro-carriers) in biological processes is a crucial object. Cell culture techniques consequently have to meet very high requirements, in particular when cultivating sensitive mammal cells. This is illustrated, for example, in the article "Langzeitkultivierung von Saügetierzellen" ("Long-term cultivation of mammal cells") in Technische Rundschau SULZER 3, 1990, pp. 24–28, in which a perfusion reactor with a rotating spin filter (MBR Spinferm Bioreaktor) is also described as the most recent prior art. The purpose of separating cells and medium is to retain cells in the bioreactor in order to achieve high cell densities, to continuously pass fresh nutrient medium through the cells and at the same time remove the product and toxic metabolites and simplify the processing of the active substances such as hormones, antibodies or vaccines, which nee separated from the cells and which have to be drawn off free from cells. The highly sensitive mammal cells have to be kept constantly in an optimum environment with a sufficient supply of nutrients and, in particular, oxygen, Absolute sterility must be maintained in the entire reaction area, while the cells, which are highly sensitive to shear forces, must not be exposed to any high mechanical stresses. Although the described perfusion reactors with a rotating spin screen represent a significant improvement on conventional filter and separating systems, cells even accumulate on the rotating screen of these reactors. This ultimately leads to clogging of the screen and the accumulation of dead, decomposing cells. Although coarser spin filters reduce the degree of clogging, the selectivity of the separation is at the same time impaired. External centrifuges are hardly suitable for separating sensitive cells on account of long feed lines, restricted oxygen supply, excessive mechanical stresses and insufficient sterility as regards the seals of moving parts.

SUMMARY OF THE INVENTION

The object of the invention is to overcome the described limitations and disadvantages of previous cell culture techniques and provide a device and a method which are particularly suitable for the long-term cultivation of sensitive mammal cells and permit a high separating effect, without the device becoming clogged, and high cell densities and thus high productivity. In keeping with these objects and with others which will become apparent hereinafter, one feature of the present invention resides, briefly stated, in a device with a rotating separating element for conveying and separating a suspension with biological cells or micro-organisms in biological processes, characterized in that the separating element comprises an inner and an outer boundary surface, which surfaces enclose a flow space which is in the form of a rotational gap and comprises an inlet opening, an inner outlet opening for the largely cell-free medium, an outer through opening and an exit opening for the suspension, the distance $R4$ of the exit opening from the axis of rotation being greater than the distance $R1$ of the inlet opening, and the distance $R3$ of the through opening being greater than the distance $R2$ of the inner outlet opening from the axis of rotation.

This object is also achieved by a bioreactor with a conveying and separating device and with a reaction vessel, which encloses the reaction space, for the suspension, the inlet opening and the exit opening leading into the reaction space, with feed lines for fresh medium and other nutrients, with a removal line for cell-free medium and with a drive for the rotating separating element.

Finally, this object is also achieved by a method for conveying and separating a suspension with biological cells or micro-organisms in biological processes in a device with a rotating separating element in a surrounding reaction space, characterized in that the suspension is conveyed out of the reaction space through an inlet opening into a rotating flow space and accelerated in an acceleration area to a predeterminable centrifugal acceleration $Z1$, then passes during a predeterminable residence time $t2$ through a separation area, in which largely cell-free medium is separated from the suspension and removed via an inner outlet opening, while the remaining suspension is returned via an outer through opening and/or exit opening to the reaction space, from where the suspension is recirculated into the inlet opening. The flow space, which is in the form of a rotational gap, and the separation distance between the inner outlet opening and the outer through opening enable the suspension to be gently accelerated and the cells separated and returned to the surrounding reaction space without delay. The separating element fulfils the following functions simultaneously, while protecting the cells as far as possible and subjecting them to minimal mechanical stress:
Rapid conveying through the device
Efficient and selective separation of cells and medium intermixing action in the surrounding space.

The object in question is solved by the simultaneous combined effect of these three functions.

The further features of the present invention provided for particularly simple arrangements, particularly gentle treatment of the cells, which can easily be optimised, adaptability to certain bioprocesses of cell types, a particularly good separating effect or particularly high productivity and cell densities. The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF PREFERRED EMBODIMENTS

Figure 1:
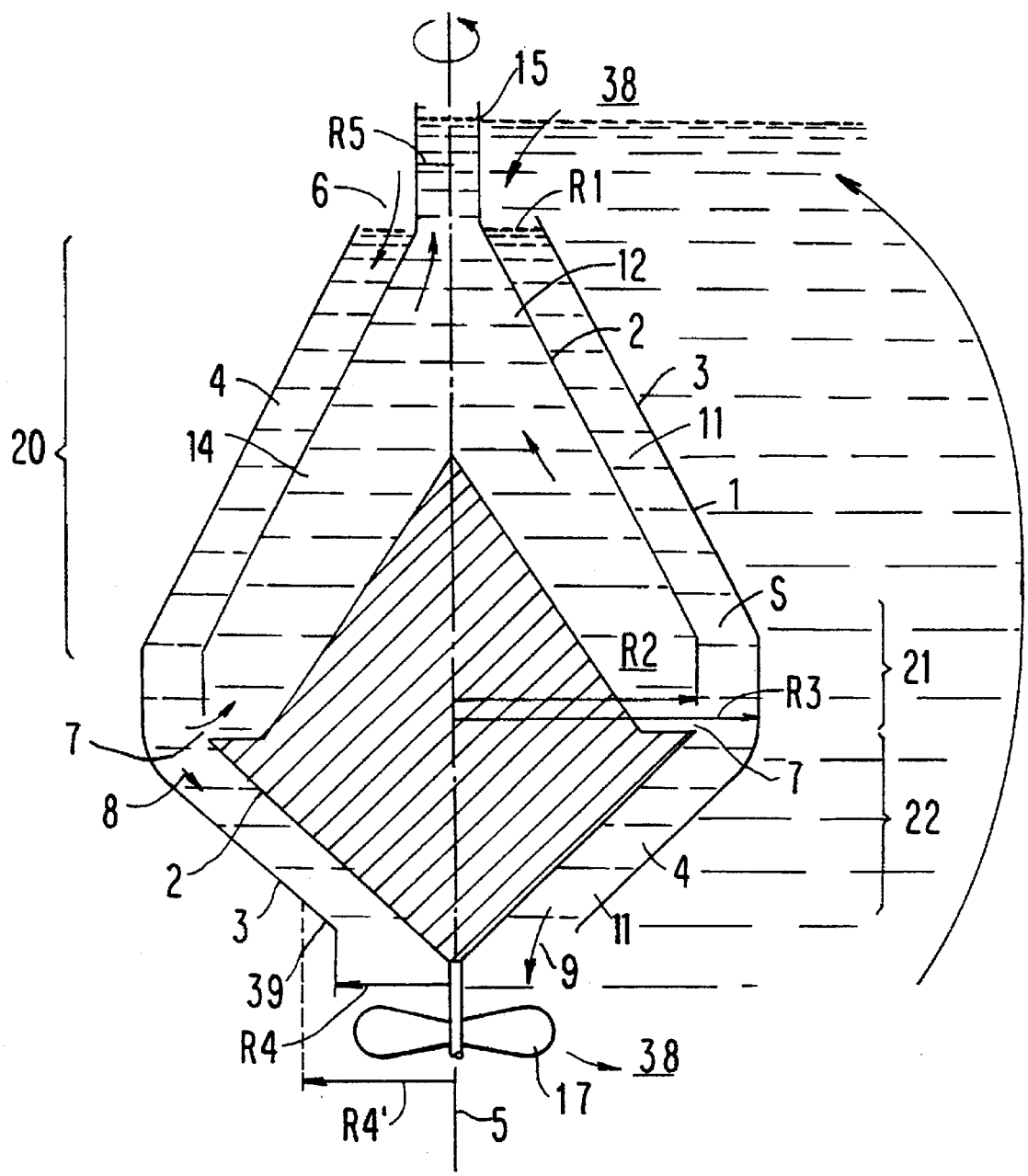
FIG. 1 is a conveying and separating device according to the invention with a flow space in the form of a rotational gap and a separate through and exit opening.

The diagrammatic conveying and separating device 1 in FIG. 1 comprises a flow space 4 for the cell suspension 11 which is in the form of a rotational gap and is formed by an inner and an outer boundary wall or boundary surface 2 and 3. The cell suspension 11 flows out of the surrounding reaction space 38 via an annular inlet opening 6 with a radius R1 into a conical acceleration area 20 of the flow space 4. The separating element 1 rotates about its axis 5. The centrifugal acceleration increases proportionally to the radius of the annular gap up to a maximum value Z1 at the point of a maximum radius R3 of an adjacent cylindrical separation space in the separation area 21. The centrifugal forces cause the cells of the suspension, which are specifically somewhat heavier, to be moved to the outer wall 3 of the flow space 4, while the lighter cell-free medium 12 remains at the inner wall 2. The largely cell-free medium 12 is drawn off via an inner outlet opening 7 with a radius R2 at the end of the separation area 21, while the suspension 11 is conveyed via the through opening 8 with a radius R3 into a conical discharge area 22, where the centrifugal acceleration is reduced as the radius decreases, up to the exit opening 9 with a radius R4, through which the suspension returns to the surrounding space 38. The cell-free medium 12 is drawn off via an inner return flow space 14 and a central removal line 15 with a radius R5.

The different radii R2 and R3 define a separation distance S=R3–R2, in which the separation of coils and cell-free medium develops. The centrifugal forces required for this are achieved by selecting the radii R and adjusting the rotational speed. R3 also determines the maximum centrifugal acceleration $Z1=\omega^2 \cdot R3$. The separation distance S is preferably between 0.1 and 0.3 R3. The exit radius R4 is greater than the inlet radius R1, thus producing a centrifugal pumping action for conveying the suspension in the flow space 4 and circulating it in the surrounding reaction space 38. The flow rate of the suspension 11 is essentially higher, by more than one order of magnitude, than that of the medium 12 which is drawn off. The openings 7 and 8 are also dimensioned accordingly. An advantage lies in the fact that the cross sections of the openings 6, 8 and 9 do not form any significant constrictions, so that there are no acceleration peaks or turbulence in the suspension. The conveying rate can, however, also be influenced to a lesser degree by these opening cross sections. These openings may preferably be formed as an annular gap, a feature which produces particularly favourable homogeneous flow conditions, although annular largely open perforated strips, for example, are also possible. The openings and holes are, however, always sufficiently large to exclude any possibility of clogging and the webs between them are so narrow that no dead angle areas in which cells might accumulate can occur behind them. Suspension (11) circulation and flow can easily be increased by means of an agitator propeller 17 near the exit opening 9, fixed on the shaft 5 of the rotating separating element 1.

Figure 2A:
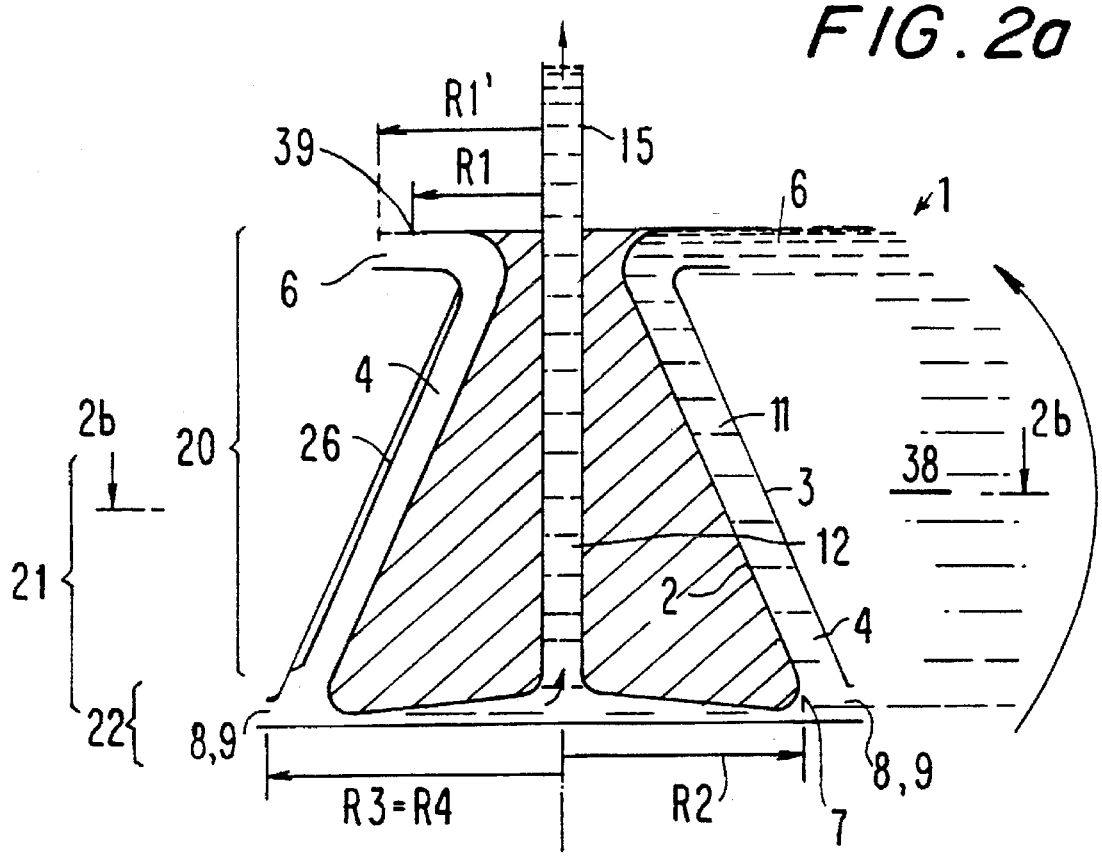
FIGS. 2a and 2b represent an example with a common exit and through opening.
Figure 2B:
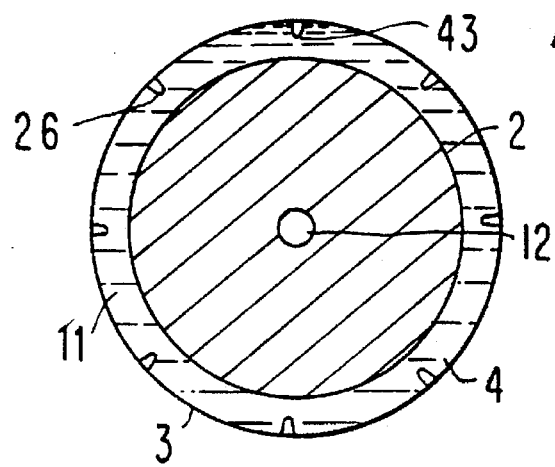

FIGS. 2a and 2b show another, very simple embodiment, in which the exit opening 9 coincides with the through opening 8. R4 and R3 are therefore of the same size, which means that the suspension can be conveyed particularly rapidly and the transit times t1 are thus short. The desired separation effect and the speed at which the suspension is conveyed in the flow space 4 is set primarily via the rotational speed of the separating element. The conveying speed is determined in particular by the radii R4 and R1 or their difference R4–R1. The exit radius R4 can be increased to R4' according to FIG. 1, for example, in order to increase the speed at which the suspension 11 is conveyed. The inlet radius R1' can, however, also be reduced to R1 instead, as shown in FIG. 2a, by replaceable annular diaphragms 39, for example. As will be explained further by the statements regarding FIG. 8, the arrangements according to FIGS. 2 and 3 result on the one hand in particularly short transit times t1 and high circulating effects in the surrounding space 38. On the other hand, however, fairly high stresses occur in the acceleration area 20 and in the discharge or retarding area 22, parts of which lie outside of the device 1 in the immediate vicinity of the openings 6 and 8.

Figure 3A:
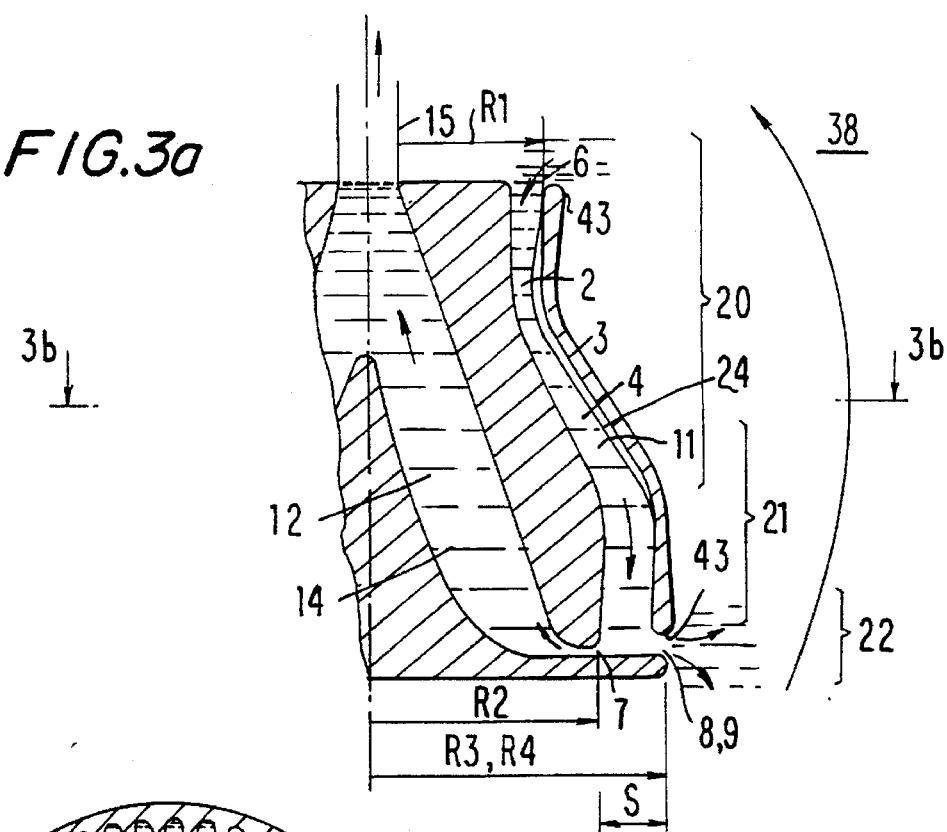
FIGS. 3a and 3b represent an example with a corrugated wall profile.
Figure 3B:
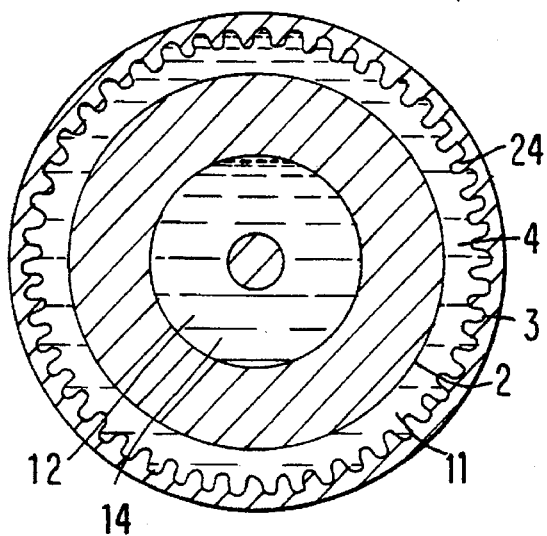
Figure 5B:
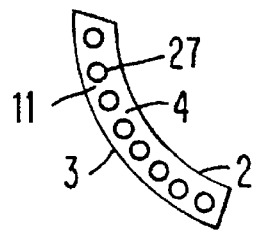
FIGS. 5a and 5b represent examples of inserts in the flow space.
Figure 5A:
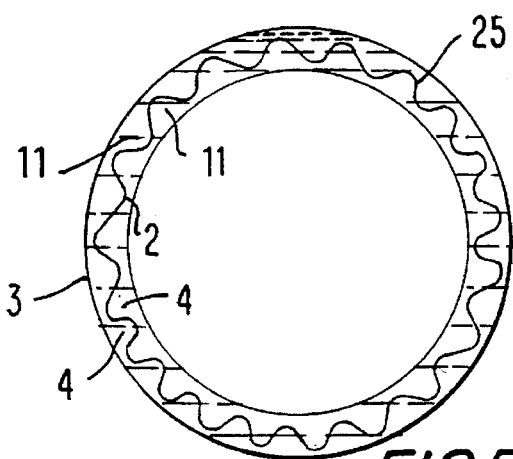
Figure 4:
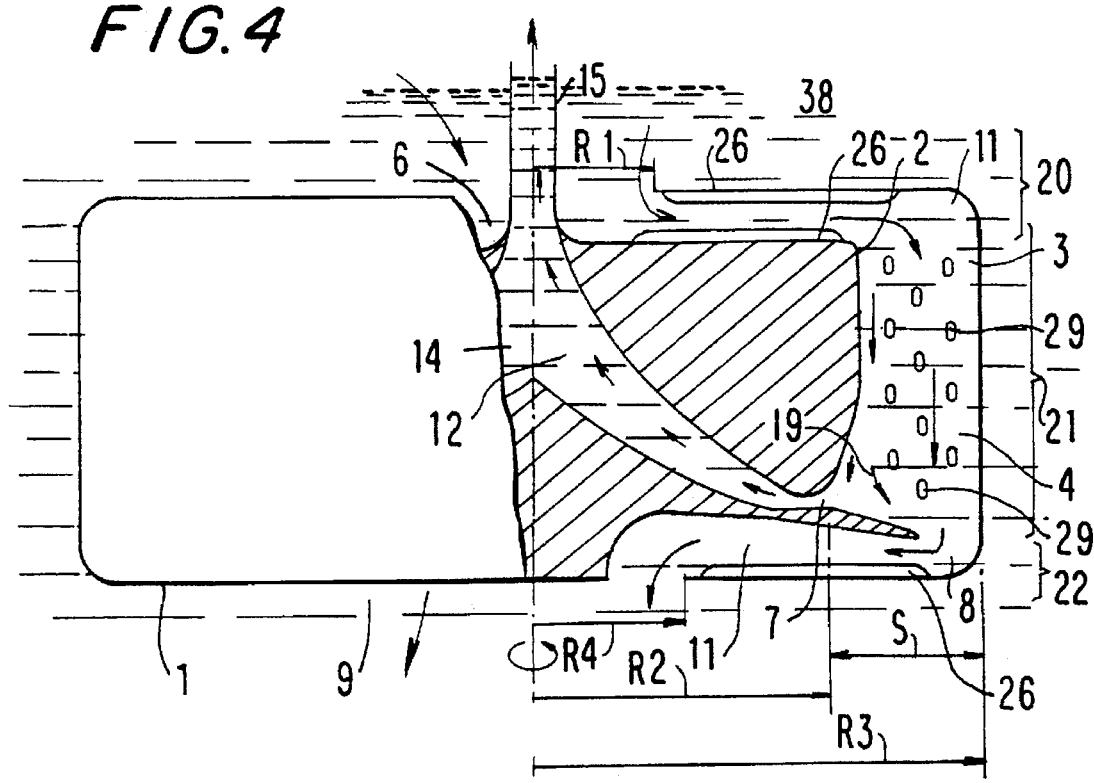
FIG. 4 represents a further example with ribs and fittings in the flow space.

FIGS. 3a and 3b show another example with a vertical inlet opening 6, a common through opening 8 and exit opening 9 and with an outer wall 3 which has a corrugated profile 24. In the example of FIGS. 2a and 2b the outer wall 3 is profiled in the form of rounded webs 26. Further examples of profiles in the flow space 4 are shown in FIG. 5a by an insert in the form of a corrugated iron sheet 25 and in FIG. 5b by round rods 27. In the example of FIG. 4 star-shaped webs 26 are mounted in the acceleration area 20 and in the discharge or retarding area 22. An annular structure Z9 is inserted in the separation area 21 in order to homogenise the suspension flow 11. These profiles, fittings and inserts in the flow space 4 are used to make the suspension flow as uniformly as possible. This should result in a uniform, turbulent-free acceleration or retardation of the suspension in the areas 20 and 22 and a relatively slow flow, which is as uniform as possible, with slight velocity gradients in the separation area 21. The flow speed is minimal and especially uniform in the area 19 before the inner outlet opening 7 in particular. The flow space 4 is shaped accordingly. For this purpose it may be composed of plane, cylindrical, conical and spherical sections. Just like the deflection parts, fittings and profiles, the openings 6, 8 and 9 are rounded (43), preferably with radii of curvature in the flow direction of at least 1 mm, in the entire suspension flow space 4.

Figure 6:
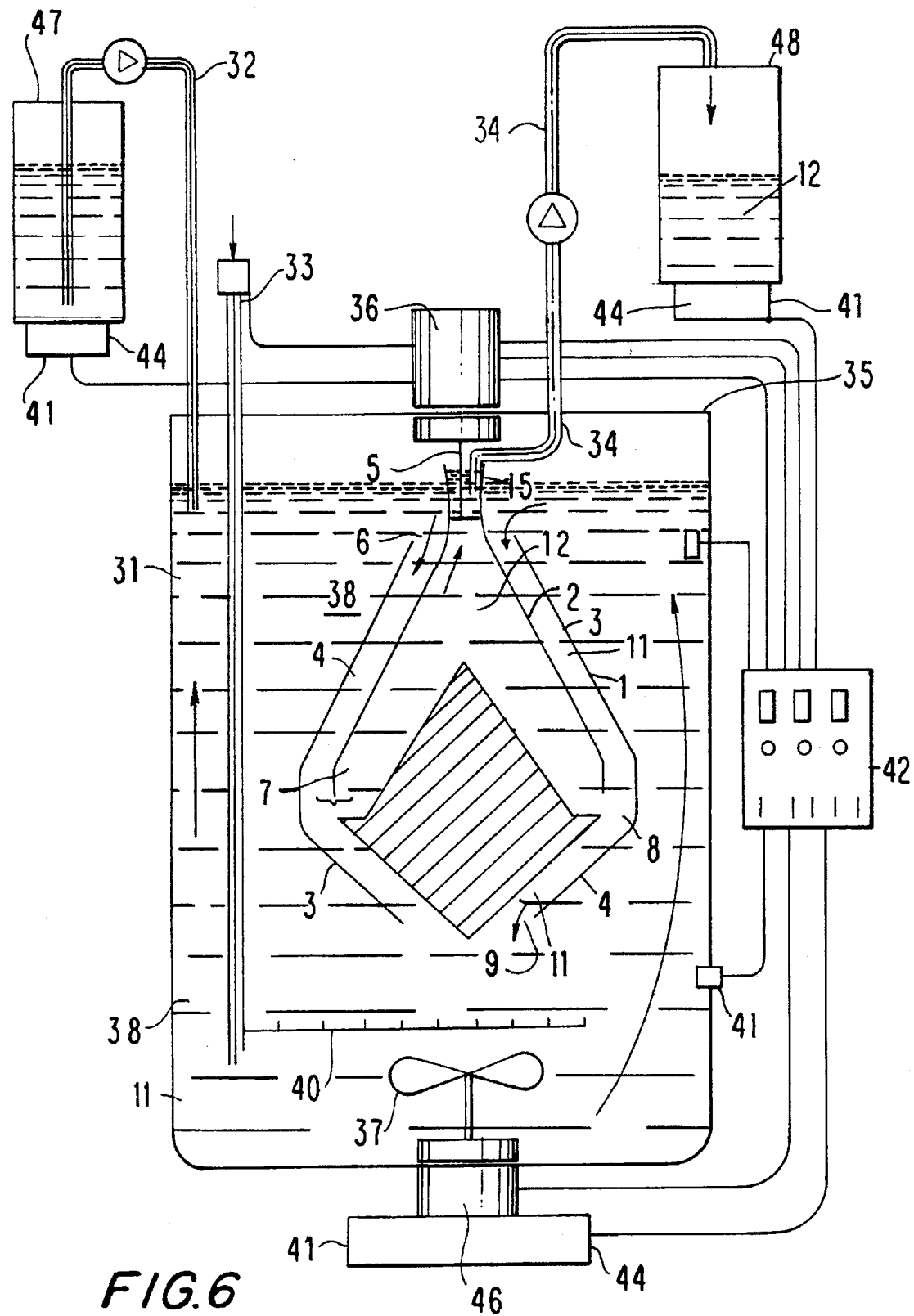
FIG. 6 is a bioreactor with a control and regulating unit.

The bioreactor according to the invention which is shown in FIG. 6 comprises a reaction vessel 31, which encloses the conveying and separating device 1 and the reaction space 38 surrounding the latter. All the lead-throughs are in this case disposed in a removable lid 35, and also in the side walls when large reactors are used. In order to achieve the best possible sterile conditions, no mobile lead-throughs are used. Drive from the external controllable motors 36, 46 is also transmitted into the sterile reaction space 38 in a non-contacting manner, e.g. via magnetic couplings, avoiding outwardly leading sliding bearing seals, which cause contamination. The cell-free medium 12 can be drawn out of the rotating discharge pipe 15 into the stationary removal line 34 in a non-contacting manner. An internal sliding bearing seal which remains sterile could also be used between the rotating discharge pipe 15 and the immobile removal line 34. A peristaltic pump is used to draw off the cell-free medium 12 in a metered manner into a collecting vessel 48. Fresh cell medium is supplied in a metered manner to the reaction space 38 from a supply vessel 47 via the feed line 32. The biological reaction can be continuously monitored and controlled in terms of quantity by means of weight sensors 44 under the supply vessel 47, the collecting vessel 48 and the reaction vessel 31 and through a defined addition of nutrients 33. A control and regulating unit 42 and, connected to the latter, further sensors 41 for temperature, cell density, concentrations and pH value are also used for this purpose. The circulation in the reaction space 38 can additionally be controlled and optimised independently of the pumping action of the separating element 1 by means of an extra, slow-running stirrer 37 with a drive 46. Oxygen is supplied, for example, by means of bubble-free aeration or through a sintered sparger 40.

Figure 7:
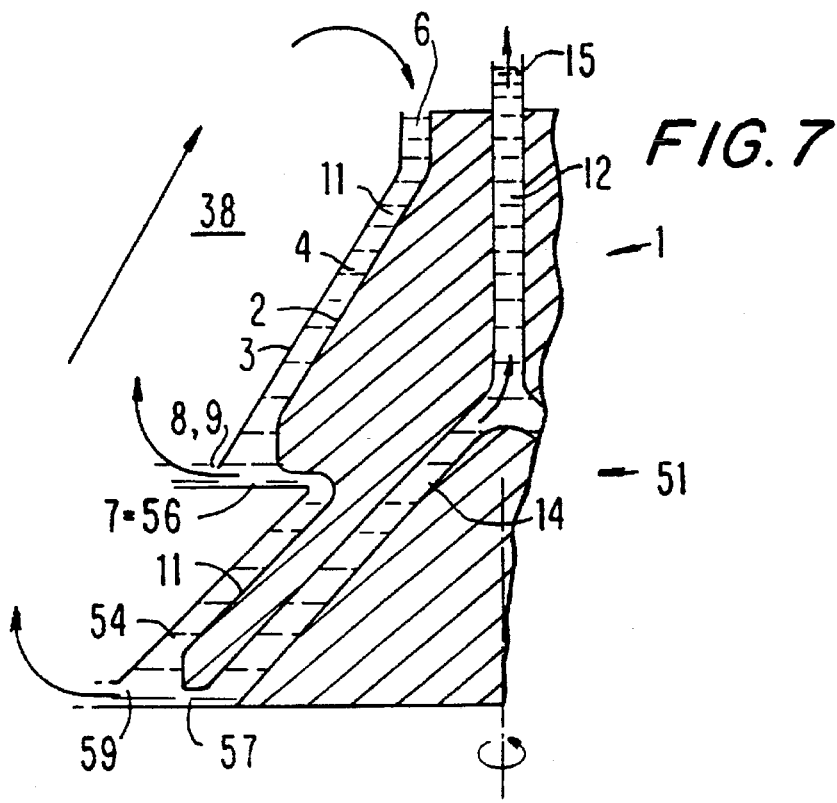
FIG. 7 is a cascade with two series-connected separating devices.

FIG. 7 shows a cascade of 2 series-connected conveying and separating devices 1 and 51 with flow spaces 4 and 54, inlet openings 6 and 56, inner exit openings 7 and 57 and exit openings 9 and 59. The inner outlet opening 7 of the first separating device simultaneously forms the inlet opening 56 of the second separating device. A particularly good separating effect is thus achieved.

Figure 8:
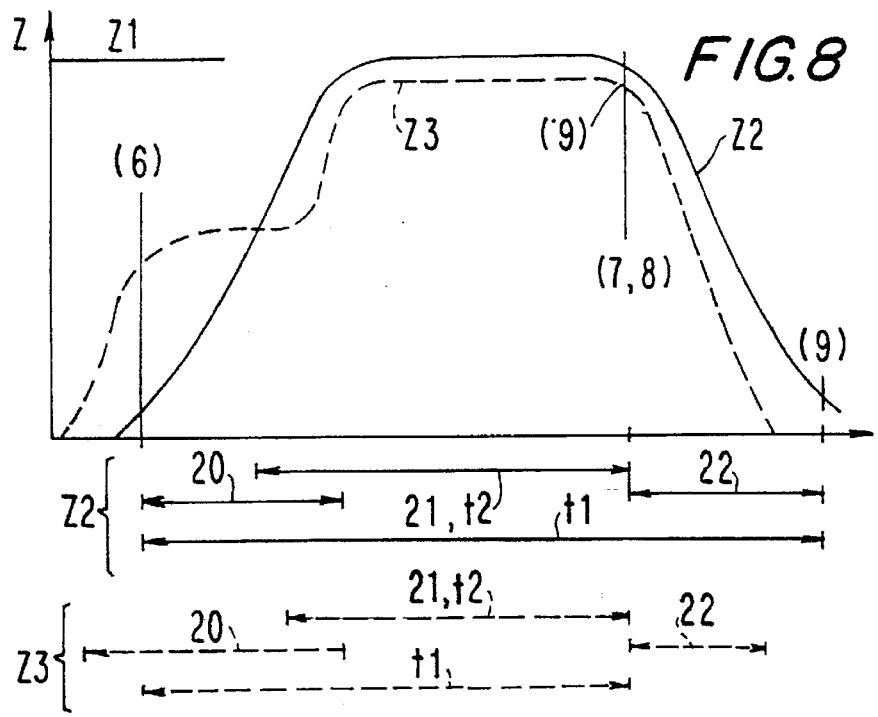
FIG. 8 shows the variation with time of the centrifugal acceleration as the cell suspension flows through the separating device.
Figure 9:
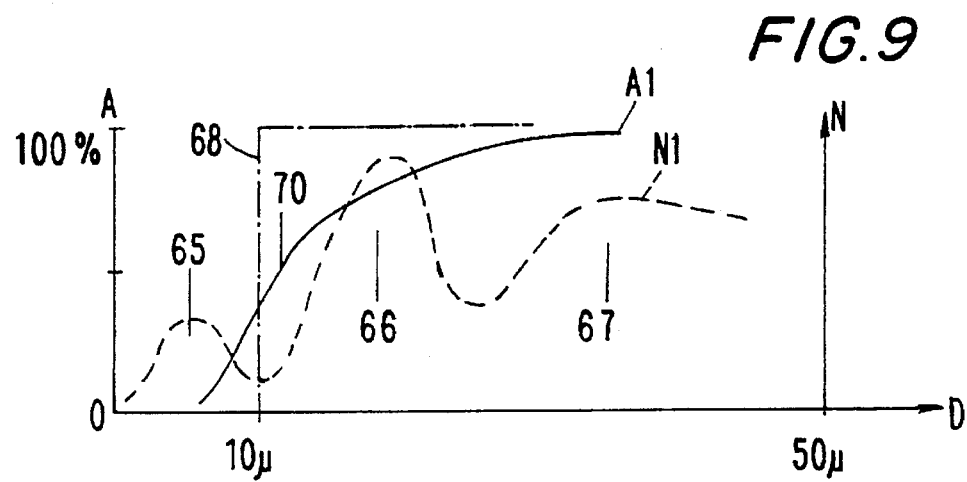
FIG. 9 it a separation curve as a function of the cell size.
Figure 10:
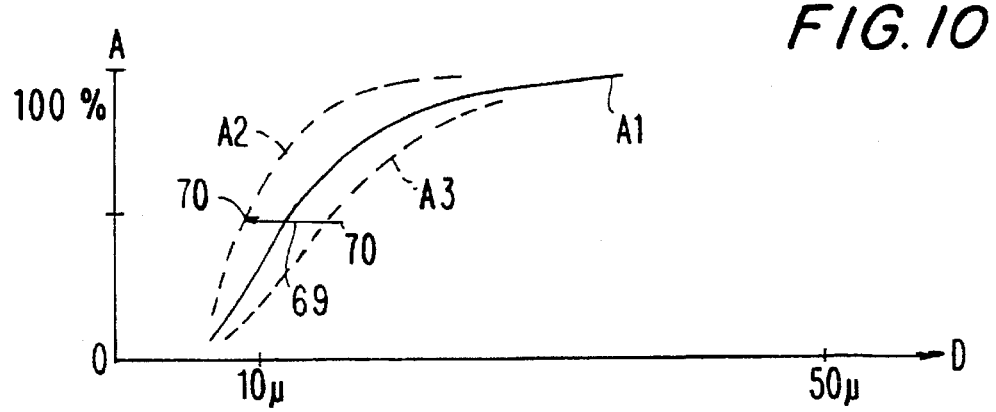
FIG. 10 represents examples of different separation curves and the displacement of the separation threshold.

The operation of the device and the method according to the invention is illustrated further in FIGS. 8 to 10. FIG. 8 shows the variation with time of the centrifugal acceleration Z, which acts on the cells the suspension 11 passes through the separating device. The curve Z2 corresponds, for example, to a device according to FIG. 1. The suspension is accelerated as uniformly as possible and without any turbulence in the acceleration area 20 after the inlet opening 6. The cells are separated during a relatively high centrifugal acceleration close to the set optimum peak value Z1 of e.g., 1–2 g, but preferably usually not move than 5 g for sensitive cells in the separation area 21, which extends up to the openings 7 and 8 is passed through in the residence time t2. This is followed by the discharge area 22 up to the exit opening 9, in which area the suspension is again retarded as gently and uniformly as possible. The transit time t1 through the entire device from the inlet opening 6 to the exit opening 9 may be relatively short, e.g. between 10 and 100 seconds, possibly up to 300 seconds. This is very important, as sensitive mammal cells can only exist for a short time without a supply of oxygen and as the nutrients can only be supplied again outside of the device 1.

In the case of the curve Z3, which corresponds to a device according to FIG. 2 or 3, the acceleration in the area 20 takes place in part before the inlet opening 6. As the openings 8 and 9 are identical here, the retarding process also take place essentially outside of the exit opening 9. The transit time t1 may be shorter than in example Z2. The residence time t2 in the area 21 may be longer than the transit time t1 in the example Z3 with a correspondingly greater separating effect. The residence time t2 may in this case lie, for example, in a range between 0.5 and 0.7 of t1. The residence time t2 represented by the curve Z2 is between 0.3 and 0.5 of t1, for example. In this case, however, particularly uniform and gentle acceleration and retardation operations are possible.

FIG. 9 shows a cell size distribution N1 of a cell line of about 20 μ average diameter, i.e. the number of cells N as a function of their size D. The bottom area 65 corresponds to dead cells, the middle area 66 to living individual cells and the top area 67 to cell aggregates. The separation curve A1 indicates the separation degree in % as a function of the cell size D. The separation threshold 70 corresponds in this case to a separation degree of 50%. Therefore, according to A1, most of the living cells 66 and 67 are separated from the dead cells 65 in the example of FIG. 9. By comparison, an ideal, unachievable separation curve 68 would correspond to a separation of all the cells of a size exceeding 10 μm, for example.

A variation in the separation curve with a displacement of the separation threshold 70 is illustrated in FIG. 10. When using the device and the method according to the invention the separation curve can be influenced by the selection of the geometric parameters such as the radii R1, R2, R3 and R4, the shape of the flow space 4, the fittings, etc. and by varying the operating parameters, i.e. particularly the rotational speed of the separating element, The optimum setting is carried out in accordance with the cell type, the biological processes and the desired product. A displacement 69 of the separation curve according to A2 with a separation threshold 70 in the case of smaller cell diameters results in a more complete separation of living cells, yet more remaining dead cells in the suspension 11. On the other hand, a displacement in the direction A3 results in a more complete separation of dead cells and a reduced retention of living cells. The separation curve may also be varied during operation. For example, in order to build up a cell population, a separation curve according to A2 may initially be set and then continuously varied in the direction of A3 as the cell population increases, regulated by means of a cell density sensor, until a maximum cell density in the suspension 11 is achieved. The cell population may, however, also be periodically collected. Long operating times can be achieved without impairing the separation characteristics.

Figure 11:
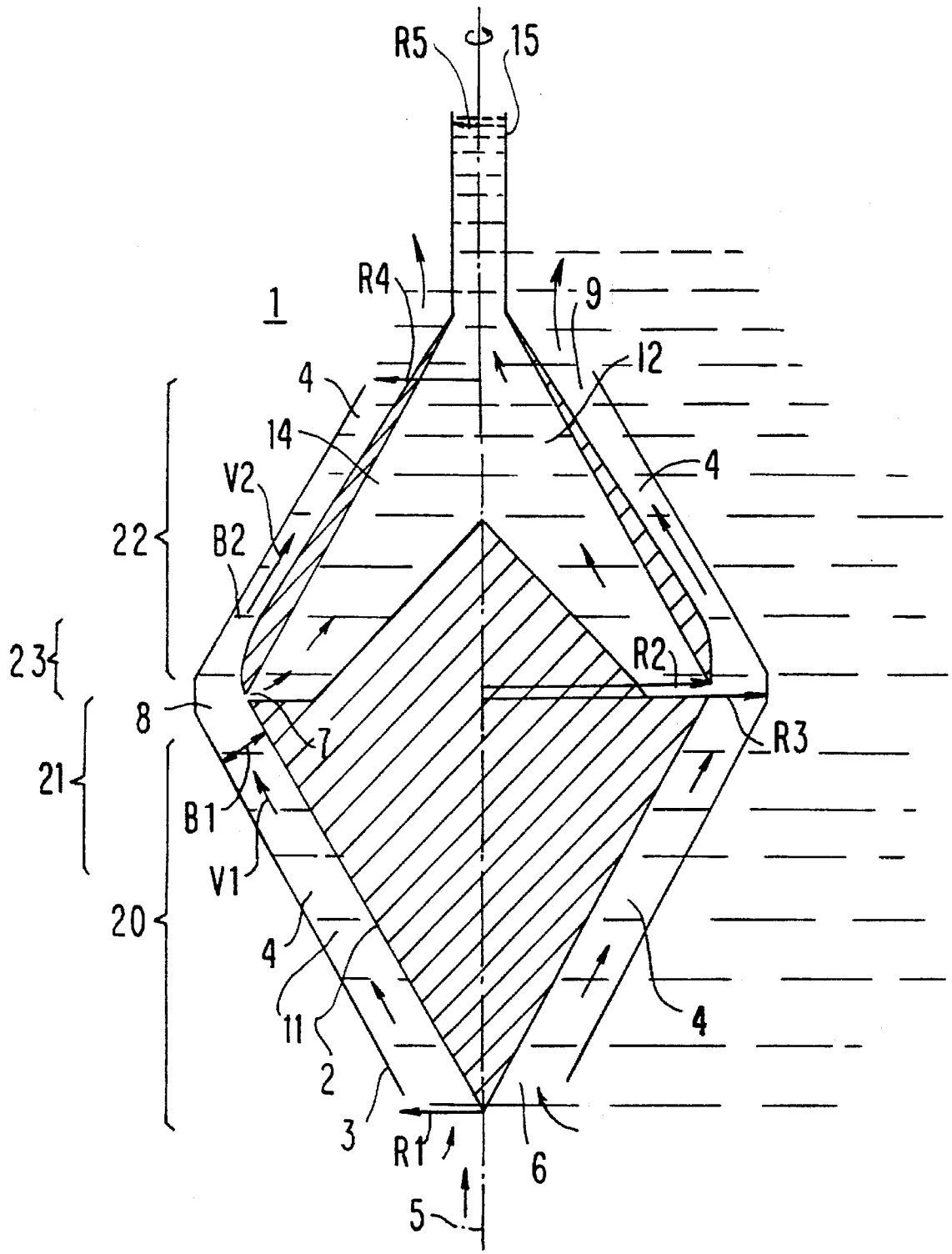
FIG. 11 is an example with the flow extending upwardly from below.

FIG. 11 shows another advantageous embodiment of the conveying and separating device according to the invention, in which the flow extends upwardly from below. At the bottom the suspension 11 enters the flow space 4 through the inlet opening 6 and leaves again at the top through the exit opening 9. The width of the rotational gap 4 so varies that the suspension flows slowly in area 21 and has a long residence time there for separation purposes and after the through opening 8 is accelerated in the area Z3 and withdrawn relatively rapidly. The width B1 of the rotational gap 4 in the separation area 21 is relatively large, so that here a correspondingly low throughflow speed V1 occurs while conversely in the area 23 and 22 the width B2 is much smaller and the speed V2 correspondingly greater.B1 is, for example, two to three times as large as B2 and V2 is correspondingly larger than V1. The entire throughflow space 4 in the form of the annular gap is also so constructed that there is nowhere a dead volume with undesirably long residence times.

The overall result of the gentle treatment by the device and the method according to the invention and of the general controllability of the separation and flow conveyance is the possibility of achieving optimum conditions, according to the cell type and the desired biological processes. Viability can thus also be increased, i.e. the proportion of dead cells is lower than that achieved by known devices.

It will be understood that each of the elements described above, or two or more together, may also find a useful application in other types of methods and constructions differing from the types described above.

While the invention has been illustrated and described as embodied in a device and a method for conveying and separating a suspension with biological cells or microorganisms, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A device for conveying suspension and separating biological cells or micro-organisms from it in biological processes, the device comprising a separating element rotatable about an axis and having an inner boundary surface and an outer boundary surface enclosing a flow space in the form of a rotational gap, said flow space having an inlet opening, an inner outlet opening for largely cell-free medium, an outer through opening and an exit opening for the suspension, said exit opening being spaced from said axis of rotation by a distance which is greater than a distance between said inlet opening and said axis, said through opening being spaced from said axis of rotation by a distance which is greater than a distance from said inner outlet opening and said axis of rotation, said flow space having an acceleration area, a separation area and a discharge area located one after the other; and a central removal line for removing the cell-free medium, said inlet opening being arranged concentrically about said central removal line, said through opening being formed substantially as an annular gap.

2. A device as defined in claim 1, wherein said distance of said through opening from said axis of rotation is greater than a distance of said exit opening from said axis of rotation.

3. A device as defined in claim 1, wherein said distance of said through opening from said axis of rotation is at least twice as great as said distance from said inlet opening to said axis of rotation.

4. A device as defined in claim 1, wherein said exit opening is identical with said through opening.

5. A device as defined in claim 1, wherein a difference between said distance of said through opening from said axis of rotation and said distance of said inner outlet opening from said axis of rotation form a separation distance, said separation distance being between 0.1 and 0.3 of said distance between said through opening and said axis of rotation.

6. A device as defined in claim 1, wherein said inner boundary surface has a conical section, a cylindrical section, a plane section and a spherically curved section located one after the other.

7. A device as defined in claim 1, wherein said outer boundary surface has a conical section, a cylindrical section, a plane section and a spherically curved section located one after the other.

8. A device as defined in claim 1, wherein each of said inner and said outer boundary surfaces has a conical section, a cylindrical section, a plane section and a spherically curved section located one after the other.

9. A device as defined in claim 1, and further comprising profiles provided in said flow space.

10. A device as defined in claim 1, and further comprising fittings provided in said flow space.

11. A device as defined in claim 1, and further comprising partitions provided in said flow space.

12. A device as defined in claim 1, wherein said boundary surfaces are formed by walls having corrugated profiles.

13. A device as defined in claim 1, and further comprising ribs provided in said flow space.

14. A device as defined in claim 1, and further comprising rods provided in said flow space.

15. A device as defined in claim 1, and further comprising rings provided in said flow space.

16. A device as defined in claim 1, and further comprising profiles provided in said flow space, said openings having boundaries, said boundaries of said openings and said profiles being rounded in a flow direction with a radius of curvature of at least 1 mm.

17. A device as defined in claim 1, wherein said openings are arranged so that a flow in said flow space extends upwardly from below.

18. A bioreactor, comprising a reaction vessel which encloses a reaction space for a suspension; a conveying and separating device for conveying the suspension and separating biological cells or microrganisms from it, and including a separating element rotatable about an axis and having an inner boundary surface and an outer boundary surface enclosing a flow space in the form of a rotational gap, said flow space having an outlet opening, an inner outlet opening for largely cell-free medium, an outer through opening and an exit opening for the suspension, said exit opening being spaced from said axis of rotation by a distance which is greater than a distance between said inlet opening and said axis, said through opening being spaced from said axis of rotation by a distance which is greater than a distance from said inner outlet opening and said axis of rotation, said inlet opening and said exit opening leading into said reaction space; feed lines for fresh medium and other nutrients; a removal line for cell-free medium; and a drive for rotating said separating element, said flow space having an acceleration area, a separation area and a discharge area located one after the other, and a central removal line for removing the cell-free medium, said inlet opening being arranged concentrically about said central removal line, said through opening being formed substantially as an annular gap.

19. A bioreactor as defined in claim 18, and further comprising a controllable stirrer arranged in said reaction space of said conveying and separating device.

20. A bioreactor as defined in claim 18, and further comprising a second conveying and separating device which is similar to said first mentioned conveying and separating device, said conveying and separating devices being series-conducted so as to form a cascade.

21. A bioreactor as defined in claim 18, and further comprising sensing means for sensing parameters of a bioreaction; and controlling means connected to said sensors and said drive so as to control said drive.

22. A bioreactor as defined in claim 21, wherein said sensing means includes sensors for temperatures, material concentrations, weight, cell density, and level.

23. A method of conveying and separating a suspension with biological cells or micro-organisms in biological processes in a device with a rotating separating element in a surrounding reaction space, the method comprising the steps of conveying the suspension out of the reaction space through an inlet opening into a rotating flow space, said flow space having an acceleration area, a separation area and a discharge area located one after the other; accelerating the suspension in the acceleration area to be a predetermined centrifugal acceleration; passing the suspension thereafter during a predetermined residence time through the separation area in which largely cell-free medium is separated from the suspension and removed via an outlet opening; returning the remaining suspension via at least one of an outer through opening and an exit opening to the reaction space from where the suspension is recirculated into the inlet opening.

said through opening being formed substantially as an annular gap; and removing the cell-free medium through a central removal line such that the inlet opening is arranged concentrically about the central removal line.

24. A method as defined in claim 23, wherein said accelerating includes a maximum centrifugal acceleration between one 1 g and 5 g.

25. A method as defined in claim 23, and further comprising the step of selecting a transit time for the suspension from the inlet opening to the exit opening between 10 and 300 seconds.

26. A method as defined in claim 25, and further comprising selecting the residence time in the separation area as a fraction of 0.3 to 0.7 of the transmit time.

27. A method as defined in claim 23, and further comprising regulating the cell density in the reaction space by detecting the cell density by means of a sensor and regulating a rotational speed of the rotating separating element.

28. A method as defined in claim 27, and further comprising the step of varying a separation threshold in continuous operation by controlling the rotational speed of the rotating separating element.

* * * * *

UNITED STATES PATENT AND TRADEMARK OFFICE
CERTIFICATE OF CORRECTION

PATENT NO. : 5,637,496
DATED : June 10, 1997
INVENTOR(S) : Thaler, et al

It is certified that error appears in the above-identified patent and that said Letters Patent is hereby corrected as shown below:

On the title page, item [73] Assignee: should read -- B. Braun Biotech International GmbH --

Signed and Sealed this

Fourteenth Day of April, 1998

Attest:

BRUCE LEHMAN

*Attesting Officer*      *Commissioner of Patents and Trademarks*